US012333723B2

(12) United States Patent
Kim

(10) Patent No.: US 12,333,723 B2
(45) Date of Patent: Jun. 17, 2025

(54) METHOD AND SYSTEM FOR COMPUTING SYNTAX SCORE USING CARDIO ANGIOGRAM

(71) Applicant: Medipixel, Inc., Seoul (KR)

(72) Inventor: Young Eon Kim, Seoul (KR)

(73) Assignee: Medipixel, Inc., Seoul (KR)

( * ) Notice: Subject to any disclaimer, the term of this patent is extended or adjusted under 35 U.S.C. 154(b) by 0 days.

(21) Appl. No.: 18/812,179

(22) Filed: Aug. 22, 2024

(65) Prior Publication Data

US 2024/0412365 A1 Dec. 12, 2024

Related U.S. Application Data

(63) Continuation of application No. PCT/KR2022/019422, filed on Dec. 1, 2022.

(30) Foreign Application Priority Data

Aug. 12, 2022 (KR) .................. 10-2022-0101538

(51) Int. Cl.
*G06K 9/00* (2022.01)
*G06T 7/00* (2017.01)
(Continued)

(52) U.S. Cl.
CPC ........... *G06T 7/0012* (2013.01); *G16H 50/30* (2018.01); *A61B 6/507* (2013.01); *G06T 2200/24* (2013.01);
(Continued)

(58) Field of Classification Search
CPC ..... G06T 2211/404; G06T 2207/30048; G06T 2207/30101; G06T 2207/20092;
(Continued)

(56) References Cited

U.S. PATENT DOCUMENTS

2007/0173719 A1* 7/2007 Haider ................. A61B 6/5247
600/431
2015/0126860 A1* 5/2015 Beymer ................ A61B 6/504
600/431
(Continued)

FOREIGN PATENT DOCUMENTS

KR 10-2015-0056866 A 5/2015
KR 10-2019-0084380 A 7/2019
WO 2014062946 A1 4/2014

*Primary Examiner* — Atiba O Fitzpatrick
(74) *Attorney, Agent, or Firm* — Banner & Witcoff, Ltd.

(57) ABSTRACT

Provided is a method for computing a SYNTAX score using a cardio angiogram, which is performed by at least one processor of a computing device, and includes acquiring an angiogram of a cardiovascular system, providing a cardiovascular segment map associated with the angiogram, in response to a user input that selects one of one or more frames included in the acquired angiogram and associates the selected one frame with a cardiovascular segment included in the cardiovascular segment map, associating the selected one frame with the cardiovascular segment, generating, using the selected one frame, an analysis result for a lesion in the associated cardiovascular segment, determining, based on the analysis result, a SYNTAX score for at least a part of the cardiovascular system, and generating an indication of the SYNTAX score.

18 Claims, 11 Drawing Sheets

(51) Int. Cl.
*G16H 50/30* (2018.01)
*A61B 6/50* (2024.01)

(52) U.S. Cl.
CPC .............. *G06T 2207/20081* (2013.01); *G06T 2207/20092* (2013.01); *G06T 2207/30048* (2013.01); *G06T 2207/30096* (2013.01); *G06T 2207/30101* (2013.01)

(58) Field of Classification Search
CPC . G06T 2207/20104; G06T 2207/20108; G06T 2200/24; G06T 2207/20081; G06T 2207/20084; G06T 9/002; G06T 5/60; G06T 11/20–60; A61B 6/507; A61B 6/504; A61B 5/0275; A61B 5/02755; A61B 5/028; A61B 6/481; A61B 6/469; G06F 3/0482; G06F 18/214–2155; G06F 7/023; G06F 40/16; G06V 10/945; G06V 10/70; G06V 10/82; G06V 10/774–7796; G06V 10/454; G06K 9/6256; G06K 9/6257; G06K 9/6259; G06N 3/02–126; G06N 20/00–20; G01N 29/4481
See application file for complete search history.

(56) References Cited

U.S. PATENT DOCUMENTS

| | | | |
|---|---|---|---|
| 2017/0322684 A1* | 11/2017 | Hermosillo Valadez | G16H 10/20 |
| 2018/0165867 A1* | 6/2018 | Kuhn | G06T 15/00 |
| 2020/0334821 A1* | 10/2020 | Schmaler | G06T 7/0012 |
| 2020/0394800 A1* | 12/2020 | Hsieh | A61B 6/504 |
| 2021/0012901 A1* | 1/2021 | Hsieh | G16H 50/50 |
| 2022/0335612 A1* | 10/2022 | Bruch-El | A61B 5/02028 |
| 2022/0392065 A1* | 12/2022 | Min | A61B 6/481 |
| 2023/0131555 A1* | 4/2023 | Inoue | G06V 10/56 382/128 |

* cited by examiner

METHOD AND SYSTEM FOR COMPUTING SYNTAX SCORE USING CARDIO ANGIOGRAM

CROSS-REFERENCE TO RELATED APPLICATIONS

This application is a continuation of International Patent Application No. PCT/KR2022/019422 filed on Dec. 1, 2022, which is based upon and claims the benefit of priority to Korean Patent Application No. 10-2022-0101538, filed on Aug. 12, 2022. The disclosures of the above-listed applications are hereby incorporated by reference herein in their entirety.

TECHNICAL FIELD

The present disclosure relates to a method and a system for computing a SYNTAX score using a cardio angiogram, and specifically, to a method and a system for computing a SYNTAX score based on a result of analyzing a lesion in a cardiovascular segment using a cardiovascular segment map associated with the cardio angiogram.

BACKGROUND

SYNTAX score is known as an independent predictor of major adverse cardiac events (MACE) for patients undergoing coronary intervention. The SYNTAX score can be used to screen high-risk groups for adverse cardiac events and help determine appropriate treatment methods. In order to calculate the SYNTAX score, it is necessary to select the image to be used for the analysis of cardiovascular lesion directly based on a plurality of cardio angiograms, divide cardiovascular regions, and then divide the cardiovascular region into cardiovascular segments. The SYNTAX score may be computed by performing several steps of questions and answers based on the information acquired in this process.

In order to accurately diagnose the patient's condition, it may be required to refer to a plurality of cardiovascular images taken from various angles for the same patient, because the clarity of images showing specific cardiovascular segments or specific lesions may differ depending on the angle from which they are taken. For this reason, it takes a lot of time and effort to compute the SYNTAX score. This causes a problem that it is difficult to quickly diagnose the patient's condition.

Additionally, along the several processes performed to compute the SYNTAX score, it is necessary to record from which angle a specific cardio angiogram is taken, which cardio angiogram, among a plurality of cardio angiograms, is used to analyze a specific cardiovascular segment, etc., but there is a problem that there is no proper tool to support this work.

SUMMARY

In order to solve one or more problems (e.g., the problems described above and/or other problems not explicitly described herein), the present disclosure provides a method for computing a SYNTAX score using a cardio angiogram, a computer program stored in a recording medium, and a device (system) including the same.

The present disclosure may be implemented in various ways, including a computer-readable non-transitory recording medium in which methods, devices, or instructions are recorded.

According to an embodiment of the present disclosure, A method for computing a SYNTAX score using a cardio angiogram may be performed by at least one processor of a computing device and include acquiring an angiogram of a cardiovascular system, providing a cardiovascular segment map associated with the angiogram, in response to a user input that selects one of one or more frames included in the acquired angiogram and associates the selected one frame with a cardiovascular segment included in the cardiovascular segment map, associating the selected one frame with the cardiovascular segment, generating, using the selected one frame, an analysis result for a lesion in the associated cardiovascular segment, determining, based on the analysis result, a SYNTAX score for at least a part of the cardiovascular system, and generating an indication of the SYNTAX score.

The providing the cardiovascular segment map may include determining, based on the acquired angiogram, an anatomical dominance of the angiogram, and providing a cardiovascular segment map associated with the anatomical dominance of the angiogram.

The determining the anatomical dominance of the angiogram may include determining, based on the acquired angiogram, the anatomical dominance of the angiogram using a machine learning model trained to determine an anatomical dominance of a given angiogram.

The determining the SYNTAX score may include generating an analysis result for a lesion in each of one or more sub-segments of the associated cardiovascular segment, and determining, based on the generated analysis result, a SYNTAX score for at least a part of the cardiovascular system.

The determining the SYNTAX score may include in response to determining that the lesion in the cardiovascular segment includes chronic total occlusion (CTO), analyzing the lesion in the associated cardiovascular segment to determine a SYNTAX score for the at least part of the cardiovascular system, without analyzing a sub-segment of the cardiovascular segment.

A method for providing a SYNTAX score using a cardio angiogram may be performed by at least one processor of a computing device and include receiving an angiogram of a cardiovascular system, outputting one or more frames included in the received angiogram, outputting a cardiovascular segment map associated with the angiogram, receiving a user input that selects one frame from among the one or more frames and associates the frame with a cardiovascular segment included in the cardiovascular segment map, in response to the user input, associating the selected frame with the cardiovascular segment, and outputting a SYNTAX score for at least a part of the cardiovascular system, in which the SYNTAX score may be determined based on a result of analyzing a lesion in the cardiovascular segment using selected one frame.

A method for providing a SYNTAX score using an angiogram may further include extracting, from the one or more frames, a frame associated with one cardiovascular segment included in the cardiovascular segment map, and outputting the extracted frame as a recommended frame of the cardiovascular segment.

The method may further include in response to determining that the selected frame and the cardiovascular segment have an association value that is equal to or less than a threshold, extracting, from the one or more frames, a frame associated with the cardiovascular segment included in the cardiovascular segment map, and outputting the extracted frame as a recommended frame of the cardiovascular segment.

The outputting the cardiovascular segment map may include outputting a cardiovascular segment map associated with an anatomical dominance of the angiogram.

The receiving the user input may include receiving a user input by a drag and drop method, in which the user input positions the selected one frame on a specific cardiovascular segment included in the cardiovascular segment map.

The outputting the SYNTAX score may include outputting the selected one frame in association with the cardiovascular segment on the cardiovascular segment map.

According to an aspect, a result of analyzing a lesion in each of one or more sub-segments of associated cardiovascular segment may be generated using selected one frame, in which the outputting the SYNTAX score may include outputting the cardiovascular segment and the one or more sub-segments, for which an analysis result of the lesion is generated, in a predetermined format.

A computer-readable non-transitory medium recording instructions that, when executed, cause performance of a method for computing a SYNTAX score using a cardio angiogram, is provided.

A computing device is provided, which may include a memory, and at least one processor coupled to the memory and configured to execute at least one computer-readable program included in the memory, in which the at least one program may include instructions that, when executed by the at least one processor, cause the computing device to acquire an angiogram of a cardiovascular system, provide a cardiovascular segment map associated with the angiogram, in response to a user input that selects one frame from among one or more frames included in the acquired angiogram and associates the selected one frame with a cardiovascular segment included in the cardiovascular segment map, associate the selected one frame with the cardiovascular segment, generate, using the selected one frame, an analysis result for a lesion in the associated cardiovascular segment, and determine, based on the analysis result, a SYNTAX score for at least a part of the cardiovascular system, and generate an indication of the SYNTAX score.

According to some aspects of the present disclosure, by associating the cardio angiogram with the cardiovascular segment and computing the SYNTAX score through analysis of the lesion in the cardiovascular segment using the cardio angiogram, it is possible to easily compute the SYNTAX score without requiring the user to compare the cardio angiogram with the cardiovascular segment on a one-to-one basis.

According to some aspects of the present disclosure, by determining the anatomical dominance based on the cardio angiogram using a machine learning model, it is possible to save the time and effort of the user to manually analyze the cardio angiogram to determine the anatomical dominance and compute the SYNTAX score.

According to some aspects of the present disclosure, the user can be recommended or notified of a frame included in the cardio angiogram associated with a specific cardiovascular segment, and thus can be assisted to associate the frame included in the cardio angiogram with the cardiovascular segment to compute the SYNTAX score.

The effects of the present disclosure are not limited to the effects described above, and other effects not described herein can be clearly understood by those of ordinary skill in the art (referred to as "ordinary technician") from the description of the claims.

BRIEF DESCRIPTION OF THE DRAWINGS

Embodiments of the present disclosure will be described with reference to the accompanying drawings described below, where similar reference numerals indicate similar elements, although the embodiments are not limited thereto.

DETAILED DESCRIPTION

Figure 1:
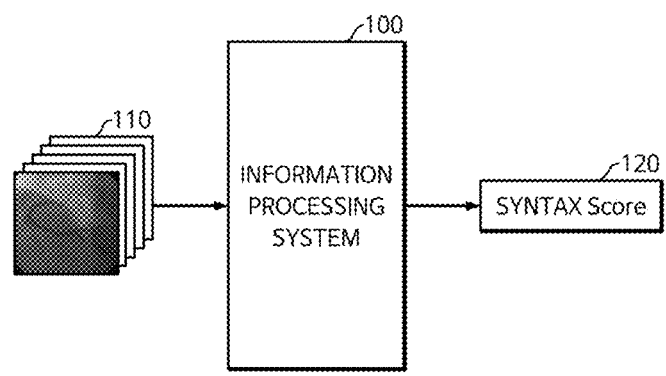
FIG. 1 is a diagram illustrating an example of a method for computing a SYNTAX score based on a cardio angiogram by an information processing system.

Hereinafter, example details for the practice of the present disclosure will be described in detail with reference to the accompanying drawings. However, in the following description, detailed description of well-known functions or configurations will be omitted when it may make the subject matter of the present disclosure rather unclear.

In the accompanying drawings, the same or corresponding components are assigned the same reference numerals. In addition, in the following description of various examples, duplicate descriptions of the same or corresponding components may be omitted. However, even if descriptions of components are omitted, it is not intended that such components are not included in any example.

Advantages and features of the disclosed examples and methods of accomplishing the same will be apparent by referring to examples described below in connection with the accompanying drawings. However, the present disclosure is not limited to the examples disclosed below, and may be implemented in various forms different from each other, and the examples are merely provided to make the present disclosure complete, and to fully disclose the scope of the disclosure to those skilled in the art to which the present disclosure pertains.

The terms used herein will be briefly described prior to describing the disclosed example(s) in detail. The terms used herein have been selected as general terms which are widely used at present in consideration of the functions of the present disclosure, and this may be altered according to the intent of an operator skilled in the art, related practice, or introduction of new technology. In addition, in specific cases, certain terms may be arbitrarily selected by the applicant, and the meaning of the terms will be described in detail in a corresponding description of the example(s). Therefore, the terms used in the present disclosure should be defined based on the meaning of the terms and the overall content of the present disclosure rather than a simple name of each of the terms.

The singular forms "a," "an," and "the" as used herein are intended to include the plural forms as well, unless the context clearly indicates the singular forms. Further, the plural forms are intended to include the singular forms as well, unless the context clearly indicates the plural forms. Further, throughout the description, when a portion is stated as "comprising (including)" a component, it is intended as meaning that the portion may additionally comprise (or include or have) another component, rather than excluding the same, unless specified to the contrary.

Further, the term "module" or "unit" used herein refers to a software or hardware component, and "module" or "unit" performs certain roles. However, the meaning of the "module" or "unit" is not limited to software or hardware. The "module" or "unit" may be configured to be in an addressable storage medium or configured to play at least one processor. Accordingly, as an example, the "module" or "unit" may include components such as software components, object-oriented software components, class components, and task components, and at least one of processes, functions, attributes, procedures, subroutines, program code segments, drivers, firmware, micro-codes, circuits, data, database, data structures, tables, arrays, and variables. Furthermore, functions provided in the components and the "modules" or "units" may be combined into a smaller number of components and "modules" or "units", or further divided into additional components and "modules" or "units."

The "module" or "unit" may be implemented as a processor and a memory. The "processor" should be interpreted broadly to encompass a general-purpose processor, a Central Processing Unit (CPU), a microprocessor, a Digital Signal Processor (DSP), a controller, a microcontroller, a state machine, etc. Under some circumstances, the "processor" may refer to an application-specific integrated circuit (ASIC), a programmable logic device (PLD), a field-programmable gate array (FPGA), etc. The "processor" may refer to a combination for processing devices, e.g., a combination of a DSP and a microprocessor, a combination of a plurality of microprocessors, a combination of one or more microprocessors in conjunction with a DSP core, or any other combination of such configurations. In addition, the "memory" should be interpreted broadly to encompass any electronic component that is capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or marking data storage, registers, etc. The memory is said to be in electronic communication with a processor if the processor can read information from and/or write information to the memory. The memory integrated with the processor is in electronic communication with the processor.

In the present disclosure, a "system" may refer to at least one of a server device and a cloud device, but is not limited thereto. For example, the system may include one or more server devices. In another example, the system may include one or more cloud devices. In still another example, the system may include both the server device and the cloud device operating in conjunction with each other.

In the present disclosure, "each of a plurality of A's" may refer to each of all components included in the plurality of A's, or may refer to each of some of the components included in the plurality of A's. For example, each of a plurality of angiograms may refer to each of all angiograms included in the plurality of angiograms or each of some angiograms included in the plurality of angiograms.

A "model" may refer to a machine learning model. For example, the "model" may refer to an artificial neural network model.

In the present disclosure, a "computing device" may refer to an information processing system or a user terminal. In addition, the computing device may refer to one or more computing devices.

FIG. 1 is a diagram illustrating an example of a method for computing a SYNTAX score based on a cardio angiogram 110 by an information processing system 100. As illustrated in FIG. 1, the information processing system 100 may refer to a system including a service for computing a SYNTAX score based on a cardio angiogram and providing the same. For example, the information processing system 100 may compute a SYNTAX score 120 corresponding to at least a part of the cardiovascular system included in the cardio angiogram 110. The SYNTAX score 120 may refer to the SYNTAX score 120 computed for each of a plurality of cardiovascular segments included in the cardio angiogram 110. Alternatively, the SYNTAX score 120 may be computed by comprehensively analyzing a plurality of cardiovascular segments included in the cardio angiogram 110. The SYNTAX score may refer to a scoring system for evaluating the complexity of coronary lesions based on anatomical features of coronary arteries. For example, the SYNTAX score may be used as independent predictors of major adverse cardiac events (MACE) for screening high-risk groups for adverse cardiac events among patients undergoing coronary intervention.

After the cardiovascular imaging of a patient with the imaging device, the cardio angiogram 110 may be input to the information processing system 100. For example, the cardio angiogram 110 may be provided to the information processing system 100 through a computing device (or a user terminal) connected to the imaging device. As another example, the cardio angiogram 110 may be provided to the information processing system 100 through a recording medium storing the cardio angiogram 110. The method for acquiring the cardio angiogram 110 by the information processing system 100 is not limited to the example described above, and any other method may be used. The cardio angiogram 110 may refer to a plurality of X-ray images of a cardiovascular system of a person, captured in one direction and/or in several directions through the imaging device.

The information processing system 100 may provide a cardiovascular segment map associated with the acquired cardio angiogram 110 to the user terminal. For example, the information processing system 100 may determine an anatomical dominance associated with the acquired cardio angiogram 110. The information processing system 100 may provide a cardiovascular segment map associated with the determined anatomical dominance to the user terminal. In this case, the anatomical dominance associated with the cardio angiogram 110 may include left dominance or right dominance. In addition, if the cardiovascular system included in the cardio angiogram 110 is determined as the left dominance, the cardiovascular segment map associated with the anatomical dominance may refer to the cardiovascular segment map associated with the left dominance. In addition, if the cardiovascular system in the cardio angiogram 110 is determined as the right dominance, the cardiovascular segment map associated with the anatomical dominance may refer to the cardiovascular segment map associated with the right dominance. The information processing system 100 may determine the anatomical dominance of the cardio angiogram based on the acquired cardio angiogram, using a machine learning model trained to determine an anatomical dominance of a given cardio angiogram.

The information processing system 100 may receive, from the user terminal, a user input to associate a cardiovascular segment included in the cardiovascular segment map with a frame included in the cardio angiogram 110. For example, the information processing system 100 may provide the user terminal with a user interface for associating the cardiovascular segment with the frame of the cardio angiogram 110, and the information processing system 100 may receive a user input from the user terminal through the user interface. To this end, a cardiovascular segment map associated with the cardio angiogram 110 may be output through the user terminal.

The user terminal may output the user interface for associating the cardiovascular segment with the frame of the cardio angiogram 110, and the information processing system 100 may receive the user input from the user terminal through the user interface. A specific example of the user interface for receiving the user input to associate the cardiovascular segment with the frame of the cardio angiogram 110 will be described below in detail with reference to FIGS. 5 to 10.

Based on the user input to associate the cardiovascular segment with the frame of the cardio angiogram 110, the information processing system 100 may generate an analysis result for a lesion in the cardiovascular segment. In addition, the information processing system 100 may compute a SYNTAX score for at least a part of the cardiovascular system based on the analysis result. With such a configuration, the SYNTAX score may be easily computed without requiring a one-to-one comparison between the cardio angiogram and the cardiovascular segment.

Figure 2:
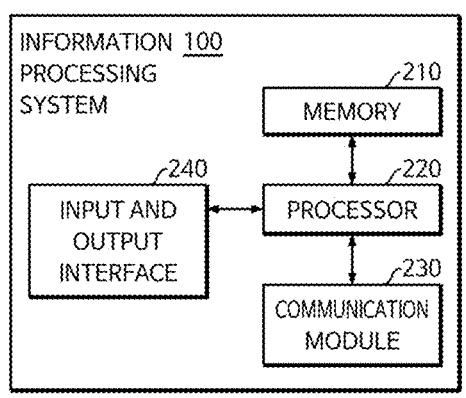
FIG. 2 is a block diagram illustrating an information processing system that provides a service for computing a SYNTAX score based on a cardio angiogram.

FIG. 2 is a block diagram illustrating the information processing system 100 that provides a service for computing a SYNTAX score based on a cardio angiogram. The information processing system 100 may include a memory 210, a processor 220, a communication module 230, and an input and output interface 240. As illustrated in FIG. 2, the information processing system 100 may be configured to communicate information and/or data through a network by using the communication module 230.

The memory 210 may include any non-transitory computer-readable recording medium. The memory 210 may include a permanent mass storage device such as disk drive, solid state drive (SSD), flash memory, etc. In another example, a non-destructive mass storage device such as ROM, SSD, flash memory, disk drive, etc. may be included in the information processing system 100 as a separate permanent storage device that is distinct from the memory. In addition, the memory 210 may store an operating system and at least one program code (e.g., installed and driven in the information processing system 100 to perform computation of a SYNTAX score computation model, computation of an anatomical dominance determination model, etc.). In FIG. 2, the memory 210 is illustrated as a single memory, but this is only for convenience of description, and the memory 210 may include a plurality of memories and/or buffer memories.

These software components may be loaded from a computer-readable recording medium separate from the memory 210. Such a separate computer-readable recording medium may include a recording medium directly connectable to the information processing system 100, and may include a computer-readable recording medium such as a floppy drive, a disk, a tape, a DVD/CD-ROM drive, a memory card, etc., for example. In another example, the software components may be loaded into the memory 210 through the communication module 230 rather than the computer-readable recording medium. For example, at least one program may be loaded into the memory 210 based on a computer program (e.g., a program, etc. for transmission of data such as angiogram of cardiovascular system) installed by the files provided by the developers, or by a file distribution system that distributes an installation file of an application through the communication module 230.

The processor 220 may be configured to process the commands of the computer program by performing basic arithmetic, logic, and input and output operations. The commands may be provided to a user terminal (not illustrated) or another external system by the memory 210 or the communication module 230. For example, the processor 220 may determine the anatomical dominance of the cardio angiogram. Based on the determined anatomical dominance, the processor 220 may provide an associated cardiovascular segment map to the user terminal, etc. Alternatively, the user terminal may select one of a plurality of pre-stored cardiovascular segment maps based on the determined anatomical dominance information and provide the selected cardiovascular segment map to the user.

The communication module 230 may provide a configuration or function for the user terminal (not illustrated) and the information processing system 100 to communicate with each other through a network, and may provide a configuration or function for the information processing system 100 to communicate with an external system (e.g., a separate cloud system). For example, control signals, commands, data, etc. provided under the control of the processor 220 of the information processing system 100 may be transmitted to the user terminal and/or the external system through the communication module 230 and the network through the communication module of the user terminal and/or an external system. For example, the information processing system 100 may receive, from the user terminal, the user input to associate the cardiovascular segment included in the cardiovascular segment map with the frame included in the cardio angiogram.

In addition, the input and output interface 240 of the information processing system 100 may be a means for interfacing with a device (not illustrated) for inputting or outputting, which may be connected to, or included in the information processing system 100. For example, the input and output interface 240 may include at least one of a PCI express interface and an Ethernet interface. In FIG. 2, the input and output interface 240 is illustrated as a separate configuration from the processor 220, but aspects are not limited thereto, and the input and output interface 240 may be configured so as to be included in the processor 220. The information processing system 100 may include more components than those illustrated in FIG. 2. Meanwhile, most of the related components may not necessarily require exact illustration.

The processor 220 of the information processing system 100 may be configured to manage, process, and/or store the information and/or data received from a plurality of user terminals and/or a plurality of external systems. The processor 220 may receive a cardio angiogram. The processor 220 may acquire a cardio angiogram. The processor 220 may provide the user terminal with a cardiovascular segment map associated with the cardio angiogram. In response to a user input that selects one of one or more frames included in the acquired cardio angiogram and associates the selected one frame with a cardiovascular segment included in the cardiovascular segment map, the processor 220 may associate the selected one frame with the cardiovascular segment. The processor 220 may generate an analysis result for the lesion in the associated cardiovascular segment using the selected one frame, and compute a SYNTAX score for at least a part of the cardiovascular system based on the analysis result.

In FIG. 2, the processor 220 is illustrated as a single processor, but this is only for convenience of description, and the processor 220 may include a plurality of processors. In addition, FIG. 2 illustrates the information processing system 100 and the user terminal separately from each other, but this is merely an example, and the service for computing SYNTAX scores may be provided through one or more computing devices integrating the information processing system 100 and the user terminal.

Figure 3:
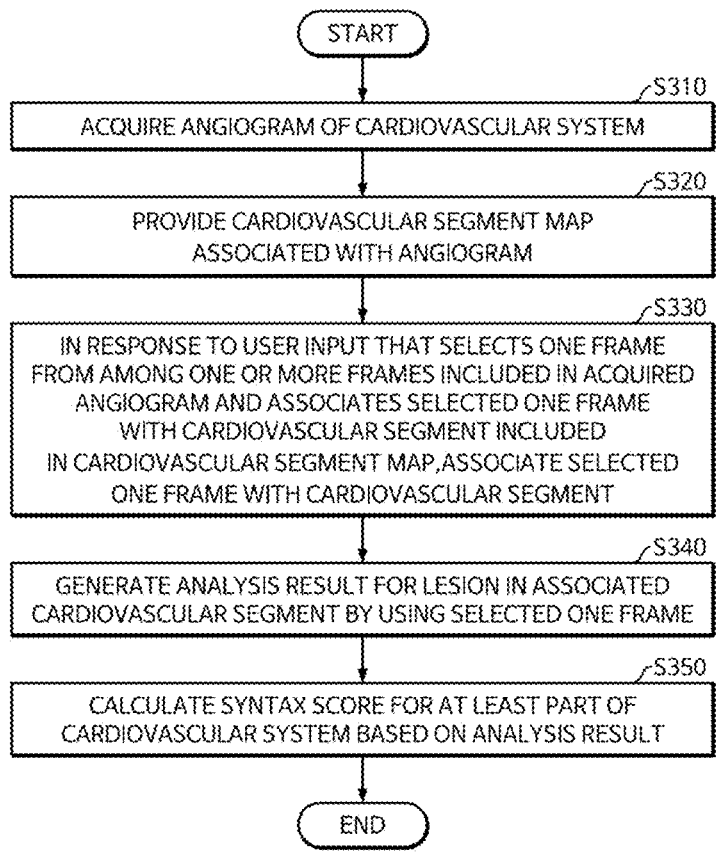
FIG. 3 is a flowchart illustrating an example of a method for computing a SYNTAX score using a cardio angiogram.

FIG. 3 is a flowchart illustrating an example of a method for computing a SYNTAX score using a cardio angiogram. The method for computing the SYNTAX score may be performed by at least one processor (e.g., the processor 220, etc. of FIG. 2) of the computing device (e.g., the information processing system 100, etc.). This method may be initiated by acquiring the angiogram of cardiovascular system, at S310. For example, the processor may acquire the angiogram by receiving the angiogram from a computing device connected to the imaging equipment capturing the angiogram and/or to any storage medium storing the angiogram.

The processor may provide a cardiovascular segment map associated with the angiogram, at S320. For example, the processor may determine the anatomical dominance of the angiogram based on the acquired angiogram. The processor may provide the cardiovascular segment map associated with the anatomical dominance of the angiogram. In this case, the anatomical dominance associated with the angiogram may include left dominance or right dominance. In addition, the cardiovascular segment map associated with the anatomical dominance may refer to a cardiovascular segment map associated with the left dominance or a cardiovascular segment map associated with the right dominance. The processor may determine the anatomical dominance of the angiogram based on the acquired angiogram, using a machine learning model trained to determine the anatomical dominance of a given angiogram.

In response to a user input that selects one of one or more frames included in the acquired angiogram and associates the selected one frame with the cardiovascular segment included in the cardiovascular segment map, the processor may associate the selected one frame with the cardiovascular segment, at S330. According to another aspect, in response to a user input that selects a plurality of frames from among the frames included in the acquired angiogram and associates the frame with the cardiovascular segment included in the cardiovascular segment map, the processor may associate one of the plurality of selected frames having the highest association score with the corresponding cardiovascular segment. To this end, the processor may compute the association score for each of the plurality of frames. The "association score" as used herein may refer to a score indicating how suitable the frame is for the analysis of a given cardiovascular segment. That is, the association score may be determined according to the size of a region in which a given cardiovascular segment is displayed in the frame, the sharpness of that region, etc.

The processor may generate an analysis result of the lesion in the associated cardiovascular segment using the selected one frame, at S340. In addition, the processor may compute a SYNTAX score for at least a part of the cardiovascular system based on the analysis result, at S350. The processor may generate an analysis result for the lesion in each of one or more sub-segments of the associated cardiovascular segment. In addition, the processor may compute the SYNTAX score for at least a part of the cardiovascular system based on the generated analysis result. In response to determining that the lesion in the cardiovascular segment includes chronic total occlusion (CTO), the processor may analyze the lesion in the associated cardiovascular segment to compute a SYNTAX score for at least a part of the cardiovascular system, without analyzing the sub-segments of the cardiovascular segment. The SYNTAX score may refer to a SYNTAX score computed for each of a plurality of cardiovascular segments included in the cardio angiogram. Alternatively, it may be a SYNTAX score computed by comprehensively analyzing some or all of a plurality of cardiovascular segments included in the cardio angiogram.

The flowchart illustrated in FIG. 3 and the above description are merely examples, and may be implemented differently in some other examples. For example, in some examples, the order of respective operations may be changed, some of the operations may be repeatedly performed, some may be omitted, or some may be added.

Figure 4:
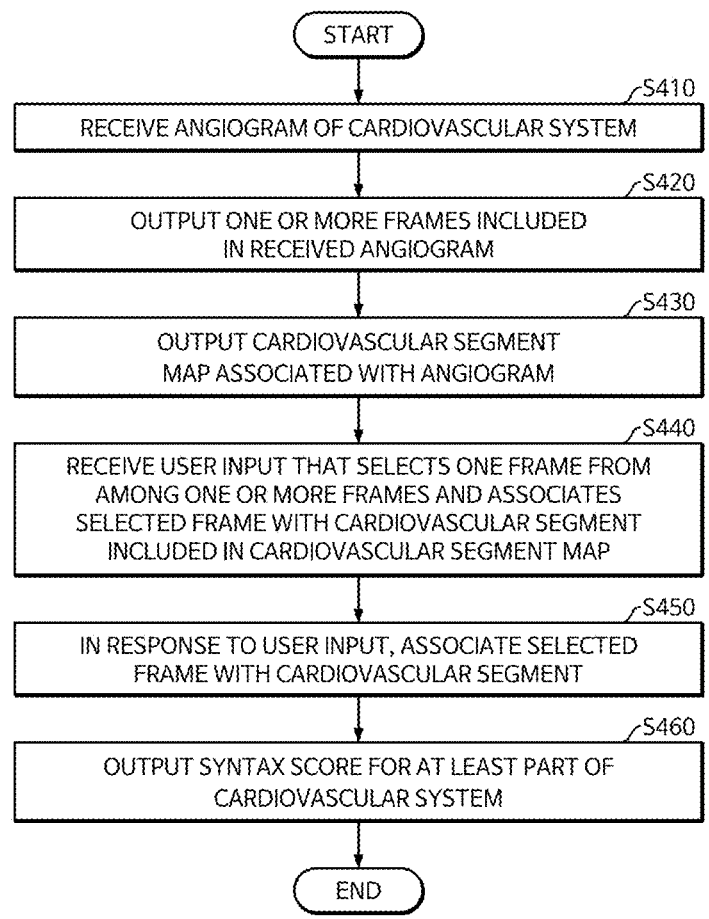
FIG. 4 is a flowchart illustrating an example of a method for providing a SYNTAX score using a cardio angiogram.

FIG. 4 is a flowchart illustrating an example of a method for providing a SYNTAX score using a cardio angiogram. The method for providing the SYNTAX score may be performed by at least one processor of a computing device (e.g., a user terminal, etc.). The method may be initiated by receiving an angiogram of cardiovascular system, at S410. For example, the processor may acquire the angiogram by receiving it through a computing device connected to the imaging device. The processor may output one or more frames included in the received angiogram, at S420.

The processor may output a cardiovascular segment map associated with the angiogram, at S430. For example, the processor may output the cardiovascular segment map associated with the anatomical dominance of the angiogram. In this case, the anatomical dominance associated with the angiogram may include left dominance or right dominance. In addition, the cardiovascular segment map associated with the anatomical dominance may refer to a cardiovascular segment map associated with the left dominance or a cardiovascular segment map associated with the right dominance. The cardiovascular segment map associated with the angiogram may be data received from the information processing system, and it may refer to a cardiovascular segment map associated with the anatomical dominance determined by the information processing system.

The processor may receive a user input that selects one frame from among one or more frames and associates the frame with the cardiovascular segment included in the cardiovascular segment map, at S440. For example, the processor may receive a user input by a drag and drop method to position the selected one frame on a specific cardiovascular segment included in the cardiovascular segment map. In response to the user input, the processor may associate the selected frame with the cardiovascular segment, at S450.

The processor may output a SYNTAX score for at least a part of the cardiovascular system, at S460. The SYNTAX score may be computed based on a result of analyzing a lesion in the cardiovascular segment using the selected one frame. In addition, the SYNTAX score may refer to a SYNTAX score computed for each of a plurality of cardiovascular segments included in the cardio angiogram. Alternatively, it may be a SYNTAX score computed by comprehensively analyzing some or all of a plurality of cardiovascular segments included in the cardio angiogram.

The processor may output, on the cardiovascular segment map, the selected one frame in association with the cardiovascular segment. For example, the processor may position the selected frame to correspond to a specific segment included in the cardiovascular segment map and output the result.

An analysis result of the lesion in each of one or more sub-segments of the cardiovascular segment associated may be generated using the selected one frame, and the processor may output the cardiovascular segment and the one or more sub-segments, for which the analysis result of the lesion is generated, in a predetermined format. The predetermined format may include a format that shows a specific segment associated with the selected frame in the same color and/or a format that shows a connecting line between the selected frame and the associated specific segment. For example, the specific segment associated with the selected frame or respective segments associated with the selected frames may be displayed and output in the same color. In another example, a connection line may be output that connects the respective segments associated with the selected frames to each other.

The processor may output a frame of a cardio angiogram having a high association with a specific cardiovascular segment included in the cardiovascular segment map as a recommended frame. Specifically, the processor may extract, from one or more frames, a frame associated with one cardiovascular segment included in the cardiovascular segment map. For example, the processor may extract, from one or more frames, a frame having an association equal to or greater than a threshold with one cardiovascular segment included in the cardiovascular segment map. The processor may output the extracted frame as a recommended frame of the cardiovascular segment.

In response to a user input to associate a frame of the angiogram with a specific cardiovascular segment included in the cardiovascular segment map, the processor may output a frame of the angiogram having a high association as a recommended frame. For example, if the frame selected by the user is not suitable for the corresponding cardiovascular segment, the processor may output another frame suitable for the corresponding cardiovascular segment as a recommended frame. Specifically, in response to determining that the selected frame and the cardiovascular segment have the association equal to or less than a threshold, the processor may extract, from one or more frames, a frame having an association equal to or greater than the threshold with the cardiovascular segment included in the cardiovascular segment map. The threshold may refer to a value of the association score described above. The processor may output the extracted frame as a recommended frame of the cardiovascular segment.

The flowchart illustrated in FIG. 4 and the above description are merely examples, and may be implemented differently in some other examples. For example, in some examples, the order of respective operations may be changed, some of the operations may be repeatedly performed, some may be omitted, or some may be added.

FIGS. 5 to 10 show user interfaces output through the display device. The user interface may be output by at least one processor of the computing device. The user interface may be connected to the user terminal to be output or controlled by at least one processor of the user terminal. In this case, the user terminal may communicate with the information processing system and output, to a display device, a user interface configured based on the information received from the information processing system. According to another aspect, the user interface may be connected to one or more computing devices including a configuration of both the information processing system and the user terminal, and may be output or controlled by at least one processor of the corresponding computing device. The display device may receive the user interface output from at least one processor and display the received user interface.

Figure 5:
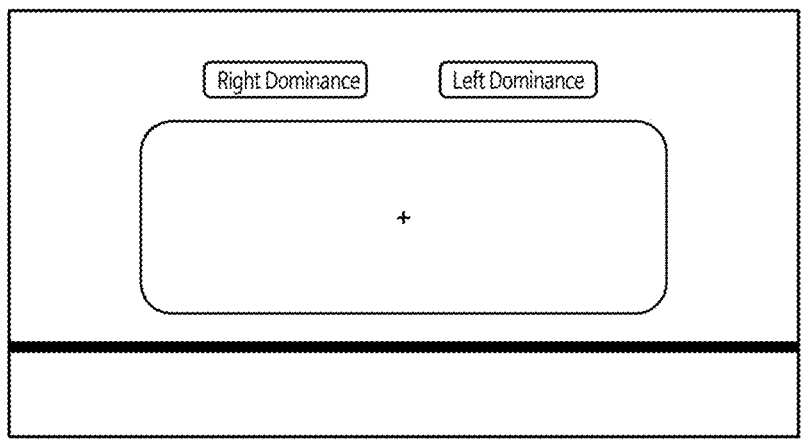
FIG. 5 is a diagram illustrating an example of outputting one or more frames included in a cardio angiogram.
Figure 5:
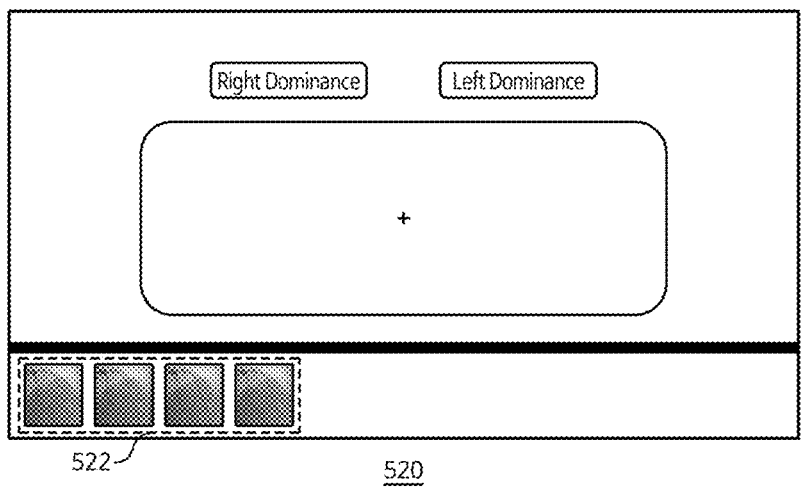

FIG. 5 is a diagram illustrating an example of outputting one or more frames included in a cardio angiogram. At least one processor of the computing device may receive a cardio angiogram and output one or more frames included in the received cardio angiogram. Each of a first user interface 510 and a second user interface 520 of FIG. 5 represents an example of an initial screen for a service for providing a SYNTAX score using a cardio angiogram, and a screen outputting one or more frames included in the cardio angiogram.

The first user interface 510 represents an example of the initial screen for the service for providing the SYNTAX score using the cardio angiogram. The second user interface 520 represents an example of the screen outputting one or more frames 522 included in the cardio angiogram. The processor may receive a cardio angiogram. The processor may output the one or more frames 522 included in the received cardio angiogram. The cardio angiogram may refer to a plurality of X-ray images obtained with an imaging device by capturing a cardiovascular system of a person in one direction and/or in several directions. As illustrated, one cardio angiogram may include the one or more frames 522. Each of the one or more frames 522 for the cardio angiogram may be displayed at a lower end of the second user interface 520.

FIG. 5 illustrates an example of displaying the one or more frames 522 included in one cardio angiogram, but aspects are not limited thereto. For example, the processor may receive a plurality of cardio angiograms obtained by capturing a person's cardiovascular system from various directions or angles, and each of one or more frames included in each of the plurality of cardio angiograms may be displayed at the bottom of the display device. In this case, the frames of the plurality of cardio angiograms may be displayed on the display and distinguishable for each of the plurality of cardio angiograms.

Figure 6:
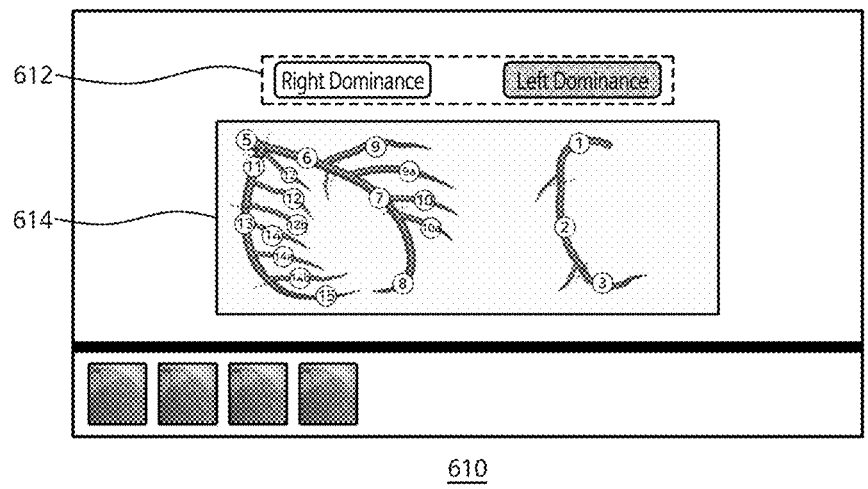
FIG. 6 is a diagram illustrating an example of a method for outputting a cardiovascular segment map associated with a cardio angiogram and associating a frame of the cardio angiogram with a cardiovascular segment of the cardiovascular segment map.
Figure 6:
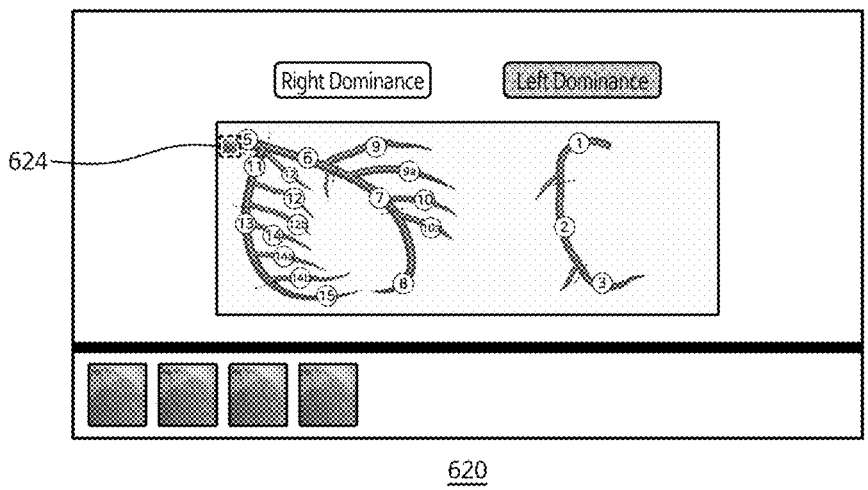

FIG. 6 is a diagram illustrating an example of a method for outputting a cardiovascular segment map 614 associated with a cardio angiogram and associating a frame of the cardio angiogram with a cardiovascular segment of the cardiovascular segment map 614. At least one processor of the computing device may output the cardiovascular segment map 614 associated with the cardio angiogram for display on the display device. In addition, the processor may output the frame of the cardio angiogram and the cardiovascular segment of the cardiovascular segment map so that they are displayed in correspondence on the display of the computing device. Each of a first user interface 610 and a second user interface 620 of FIG. 6 represents an example of a screen outputting the cardiovascular segment map 614 for the anatomical dominance associated with the cardio angiogram, and an example of a screen showing the frame of the cardio angiogram and the cardiovascular segment of the cardiovascular segment map 614 corresponding to each other.

The first user interface 610 represents the example of the screen outputting the cardiovascular segment map 614 for the anatomical dominance associated with the cardio angiogram. At least one processor of the computing device may output the cardiovascular segment map 614 associated with the cardio angiogram. Specifically, the processor may output the cardiovascular segment map 614 associated with the anatomical dominance of the cardio angiogram. In this case, the anatomical dominance associated with the cardio angiogram may include left dominance or right dominance. In addition, the cardiovascular segment map associated with the anatomical dominance may refer to a cardiovascular segment map associated with the left dominance or a cardiovascular segment map associated with the right dominance. For example, as illustrated, the processor may output a region 612 to select the right dominance "Right Dominance" and the left dominance "Left Dominance" associated with the cardio angiogram. If the left dominance "Left Dominance" is selected, the cardiovascular segment map 614 associated with the left dominance may be displayed through the display device. The cardiovascular segment map 614 may include a plurality of cardiovascular segments. Each of the plurality of cardiovascular segments may be displayed and distinguishable from each other with numbers and/or symbols.

The second user interface 620 represents an example of a screen showing a selected frame 624 of the cardio angiogram and a specific cardiovascular segment corresponding thereto. At least one processor of the computing device may receive a user input that selects one frame from among the one or more frames and associates the selected one frame with the cardiovascular segment. Specifically, the processor may receive a user input that positions, through a drag-and-drop method, the selected frame on the specific cardiovascular segment. In response to this user input, the selected frame 624 may be output to the second user interface 620 in association with the specific cardiovascular segment. For example, as illustrated, in response to a user input, the processor may output the frame 624 selected in association with the specific cardiovascular segment (e.g., "Cardiovascular Segment #5") to the second user interface 620 correspondingly at a position adjacent to the corresponding specific cardiovascular segment.

The at least one processor may output a SYNTAX score for at least a part of the cardiovascular system. The SYNTAX score may be computed based on a result of analyzing a lesion in the cardiovascular segment using the selected one frame. For example, if the analysis of the lesion for the specific cardiovascular segment (e.g., the "Cardiovascular Segment #5") corresponding to the selected frame 624 is completed, the SYNTAX score computed based on the analysis result may be output together with the selected frame 624 at a position corresponding to the corresponding specific cardiovascular segment.

Figure 7:
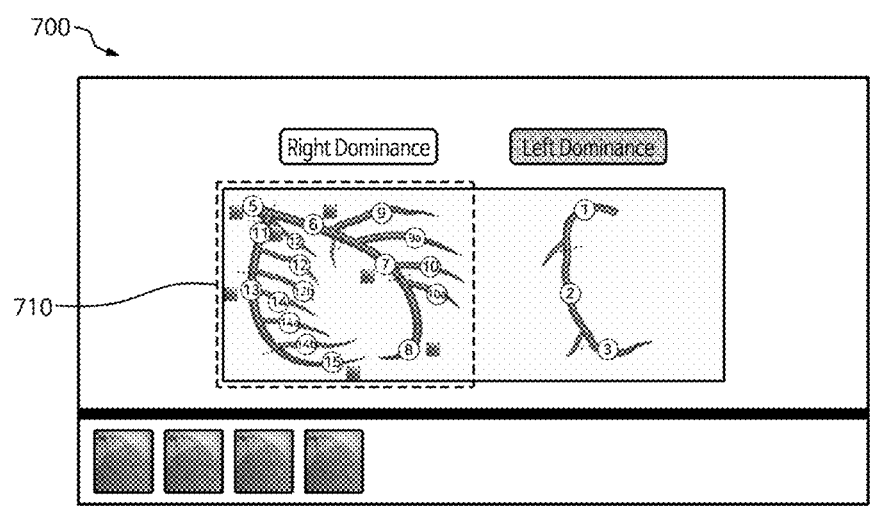
FIG. 7 is a diagram illustrating an example of a method for displaying, by a user, a specific cardiovascular segment associated with a frame and sub-segments of the specific cardiovascular segment corresponding to each other.

FIG. 7 is a diagram illustrating an example of a method for displaying, by a user, a specific cardiovascular segment associated with a frame and sub-segments of the specific cardiovascular segment corresponding to each other. If the analysis of the lesion in the sub-segment(s) of the specific cardiovascular segment associated with the frame of the cardio angiogram is completed, at least one processor of the computing device may output an analysis result 710 in association with the corresponding segment(s). For example, the processor may output, on the display, a user interface 700 displaying the analysis result 710 for the lesion in the sub-segment(s) of the specific cardiovascular segment associated with the frame of the cardio angiogram. As illustrated, the sub-segments of the "Cardiovascular Segment #5" may include "Cardiovascular Segments #6, #7, #8, #11, #13, and #15". If the analysis of the lesion in the "Cardiovascular Segment #5" and its sub-segment(s) is completed, the processor may output the analysis result 710 for the "Cardiovascular Segment #5" and its sub-segment(s) together with the frame used for the analysis. The analysis result 710 may include SYNTAX scores in the sub-segment(s) of the specific cardiovascular segment associated with the frame of the cardio angiogram.

At least one processor of the computing device may transmit the frame of the cardio angiogram and information on a cardiovascular segment associated with the same to the information processing system. The processor of the information processing system may compute a SYNTAX score based on the received frame of the cardio angiogram and information on the cardiovascular segment. For example, the processor of the information processing system may detect blood vessel regions included in the frame of the cardio angiogram, acquire a blood vessel center line, divide blood vessel segments, and perform lesion analysis.

The processor of the information processing system may detect the blood vessel region using a machine learning model trained to detect the blood vessel region in the image. For example, it may be determined whether the blood vessel region includes chronic total occlusion (CTO). As a specific example, the processor of the information processing system may acquire the center line of the blood vessel region using a Medial Axis method and divide the blood vessel region into one or more segments based on the branch structure of the center line. The processor of the information processing system may analyze the lesion in the detected blood vessel region. In addition, if it is determined that the blood vessel region includes CTO, the processor of the information processing system may extract a segment including the CTO from one or more segments. The processor of the information processing system may compute the SYNTAX score based on the information of the segment including the analyzed lesion and the CTO, etc. The computed SYNTAX score may be transmitted to the user terminal together with the information on the segment associated with the same and used to output an analysis result for the lesion in the sub-segment(s) of the specific cardiovascular segment associated with the frame of the cardio angiogram.

If analysis is automatically performed for the sub-segment(s) of the specific cardiovascular segment, and analysis is performed separately later or the lesion in the upper-level segment using another frame of the cardio angiogram, if there is a difference between the analysis results, the processor may replace the analysis result for the sub-segment(s) with the analysis result performed later and output the result. For example, if analysis is automatically performed for the "Cardiovascular Segment #6" and the "Cardiovascular Segment #9", which are sub-segments of the "Cardiovascular Segment #5", and analysis is performed separately later for the "Cardiovascular Segment #6", which is the upper-level segment of the "Cardiovascular Segment #9" upon a user input (e.g., drag-and-drop) requesting the analysis, if there is a difference between the analysis results, the analysis result of the "Cardiovascular Segment #9", which is the sub-segment of the "Cardiovascular Segment #6", may be replaced by the analysis result performed later and output.

On the other hand, if the analysis for a specific sub-segment is performed by a user input requesting the analysis of the specific sub-segment of the specific cardiovascular segment, even if the analysis of the lesion for the upper-level segment is performed separately later using another frame of the cardio angiogram, the processor may not replace the analysis result for the sub-segment(s) with the analysis result performed later and may maintain the previous analysis result. For example, if analysis for the "Cardiovascular Segment #9", which is a sub-segment of the "Cardiovascular Segment #5" is performed separately by user input (e.g., drag-and-drop) requesting the analysis, and analysis for the "Cardiovascular Segment #6", which is a upper-level segment of the "Cardiovascular Segment #9", is performed separately, the analysis result of the "Cardiovascular Segment #9" may not be replaced with the analysis result performed later, and the previous analysis result may be maintained and output.

FIG. 7 illustrates an example of outputting analysis results for "Cardiovascular Segments #6, #7, #8, #11, #13, and #15" as the sub-segments of the "Cardiovascular Segment #5", but this is for convenience of explanation and it should be noted that the results for the remaining sub-segments associated with "Cardiovascular Segment #5" are omitted. The sub-segments of the "Cardiovascular Segment #5" may include "Cardiovascular Segments #9 and #9a", which are sub-segments of "Cardiovascular Segment #6", "Cardiovascular Segment 10 and 10a", which are sub-segments of "Cardiovascular Segment #7", "Cardiovascular Segment 12a", "Cardiovascular Segment #12a and #12b", which are sub-segments of "Cardiovascular Segment #11", and "Cardiovascular Segment #14, #14a, #14b, and #15", which are sub-segments of "Cardiovascular Segment #13".

Figure 8:
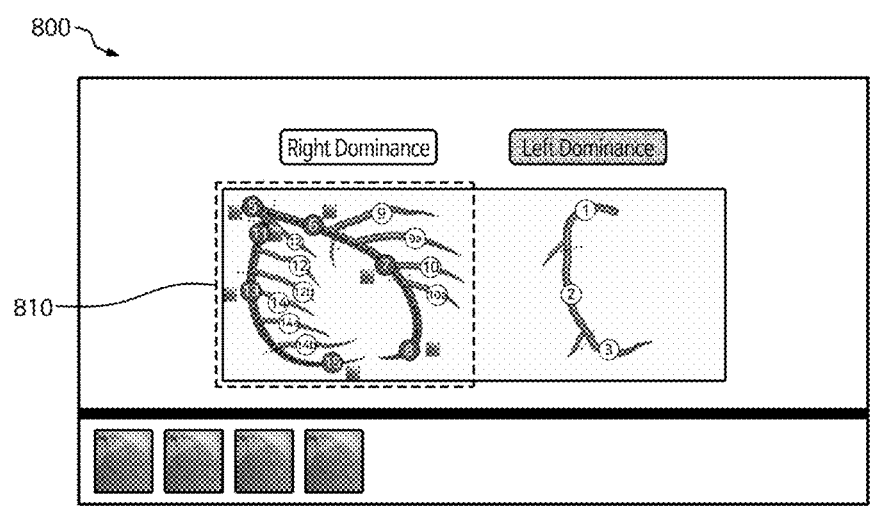
FIG. 8 is a diagram illustrating an example of a method for distinguishing and displaying an analyzed cardiovascular segment and a non-analyzed cardiovascular segment.

FIG. 8 is a diagram illustrating an example of a method for displaying an analyzed cardiovascular segment and a non-analyzed cardiovascular segment by distinguishing each other. An analysis result of a lesion in each of one or more sub-segments of the associated cardiovascular segment may be generated using the selected frame, and at least one processor of the computing device may output the cardiovascular segment and the one or more sub-segments, for which the analysis result of the lesion is generated, in a predetermined format. The predetermined format may include a format that shows a specific segment associated with the selected frame in the same color and/or a format that shows a connecting line between the selected frame and the associated specific segment. For example, one processor may output, for display through the display device, a user interface 800 displaying an analysis result 810 for some cardiovascular segments in a predetermined format. As illustrated, the sub-segments of the "Cardiovascular Segment #5" may include "Cardiovascular Segments #6, #7, #8, #11, #13, and #15". If the analysis of the lesion in the "Cardiovascular Segment #5" and its sub-segment(s) is completed, the processor may output the analysis result 810 for some cardiovascular segments in a predetermined format while indicating completion or incompletion of the analysis. The analysis result 810 may include SYNTAX scores in the sub-segment(s) of the specific cardiovascular segment associated with the frame of the cardio angiogram. For example, as illustrated, the processor may display and output the analyzed cardiovascular segments, which are completely analyzed based on the selected frame, in the same color (e.g., in gray shade). In addition, the processor may output a connection line (e.g., dotted line) connecting each of the analyzed cardiovascular segments based on the selected frames. In this case, the processor may also output a frame of the cardio angiogram associated with the corresponding cardiovascular segment together with the analysis result 810 of the analyzed cardiovascular segment.

FIG. 7 illustrates an example of outputting analysis results for "Cardiovascular Segments #6, #7, #8, #11, #13, and #15" as the sub-segments of the "Cardiovascular Segment #5", but this is for convenience of explanation and it should be noted that the results for the remaining sub-segments associated with "Cardiovascular Segment #5" are omitted. The sub-segments of the "Cardiovascular Segment #5" may include "Cardiovascular Segments #9 and #9a", which are sub-segments of "Cardiovascular Segment #6", "Cardiovascular Segment 10 and 10a", which are sub-segments of "Cardiovascular Segment #7", "Cardiovascular Segment 12a", "Cardiovascular Segment #12a and #12b", which are sub-segments of "Cardiovascular Segment #11", and "Cardiovascular Segment #14, #14a, #14b, and #15", which are sub-segments of "Cardiovascular Segment #13".

Figure 9:
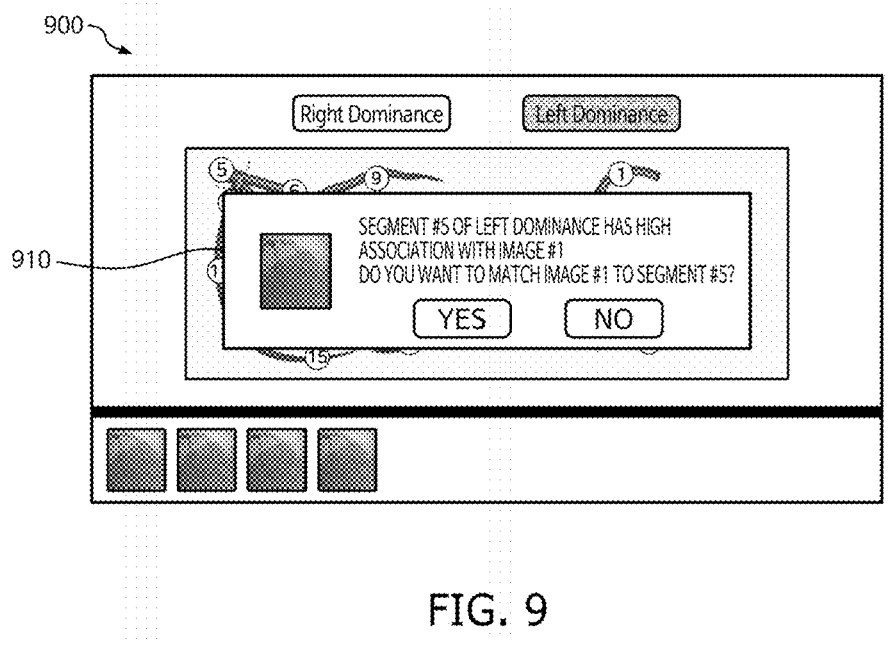
FIG. 9 is a diagram illustrating an example of recommending a frame of a cardio angiogram having a high association with a specific cardiovascular segment included in the cardiovascular segment map.

FIG. 9 is a diagram illustrating an example of a screen 900 that recommends a frame of a cardio angiogram having a high association with a specific cardiovascular segment included in a cardiovascular segment map. At least one processor of the computing device may output a frame of a cardio angiogram having a high association with a specific cardiovascular segment included in the cardiovascular segment map as a recommended frame. The "frame having the high association" may refer to one frame having the highest association score of a plurality of frames. To this end, the processor may compute an association score for each of the plurality of frames. The association score may refer to a score indicating how suitable the frame is for analysis of a given cardiovascular segment. That is, the association score may be determined according to the size of a region in which a given cardiovascular segment is displayed in the frame, the sharpness of the region, etc. For example, the processor may extract, from one or more frames, a frame associated with one cardiovascular segment included in the cardiovascular segment map. The processor may output the extracted frame as a recommended frame of the cardiovascular segment, together with a notification message 910.

For example, as illustrated, the processor may output "Frame #1" of the cardio angiogram having a high association with the "Cardiovascular Segment #5" included in the cardiovascular segment map as a recommended frame, together with the notification message 910. In response to a user input requesting an analysis of a specific cardiovascular segment (e.g., the "Cardiovascular Segment #5") with a frame (e.g., the "Frame #1") of the cardio angiogram having a high association, the processor may perform the analysis of the lesion with the recommended frame (e.g., the "Frame #1") for the specific cardiovascular segment (e.g., the "Cardiovascular Segment #5").

Figure 10:
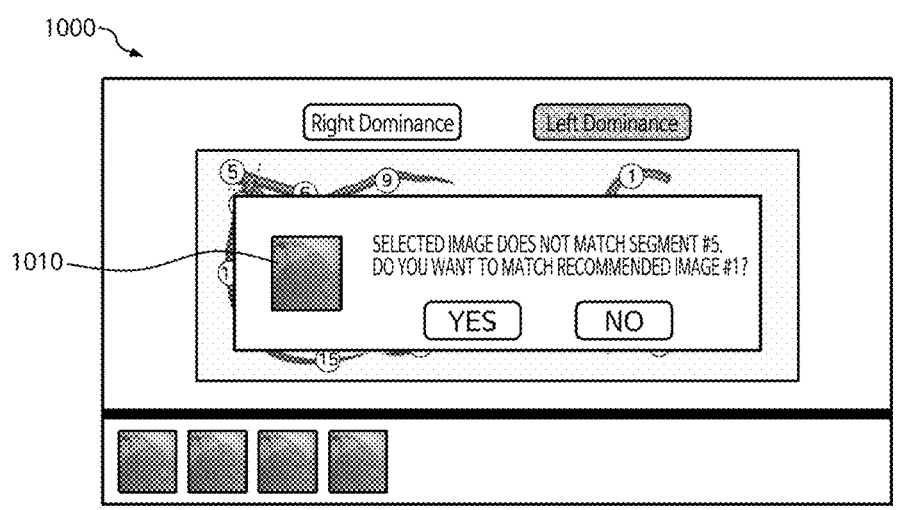
FIG. 10 is a diagram illustrating an example of recommending a frame of a cardio angiogram having a high association with a specific cardiovascular segment included in the cardiovascular segment map, according to another aspect.

FIG. 10 is a diagram illustrating an example of a screen 1000 that recommends a frame of a cardio angiogram having a high association with a specific cardiovascular segment included in a cardiovascular segment map, according to another aspect of the present disclosure. For the user input to associate the frame of the cardio angiogram with the specific cardiovascular segment included in the cardiovascular segment map, if at least one processor of the computing device determines that the frame selected by the user is not suitable for the corresponding cardiovascular segment, the processor may output another frame of the cardio angiogram having a high association as a recommended frame. Specifically, in response to determining that the frame selected by the user and the cardiovascular segment have an association equal to or less than a threshold (i.e., a threshold association score), the processor may extract, from one or more frames, a frame having a high association with the cardiovascular segment included in the cardiovascular segment map. The processor may output the extracted frame as a recommended frame of the cardiovascular segment, together with a notification message 1010. The frame of the cardio angiogram having the high association may refer to one frame having the highest association score among a plurality of frames, as described above with reference to FIG. 9.

For example, as illustrated, in response to determining that the selected frame (e.g., any frame excluding "Frame #1") and the "Cardiovascular Segment #5" have an association equal to or less than a threshold, at least one processor of the computing device may extract, from one or more frames, "Frame #1" associated with the cardiovascular segment included in the cardiovascular segment map. The processor may output the extracted "Frame #1" as a recommended frame of the cardiovascular segment together with the notification message 1010. In response to a user input requesting an analysis of the specific cardiovascular segment (e.g., the "Cardiovascular Segment #5") with the frame (e.g., the "Frame #1") of the cardio angiogram having high association, at least one processor of the computing device may perform the analysis of the lesion with the recommended frame (e.g., the "Frame #1") for the specific cardiovascular segment (e.g., the "Cardiovascular Segment #5").

Figure 11:
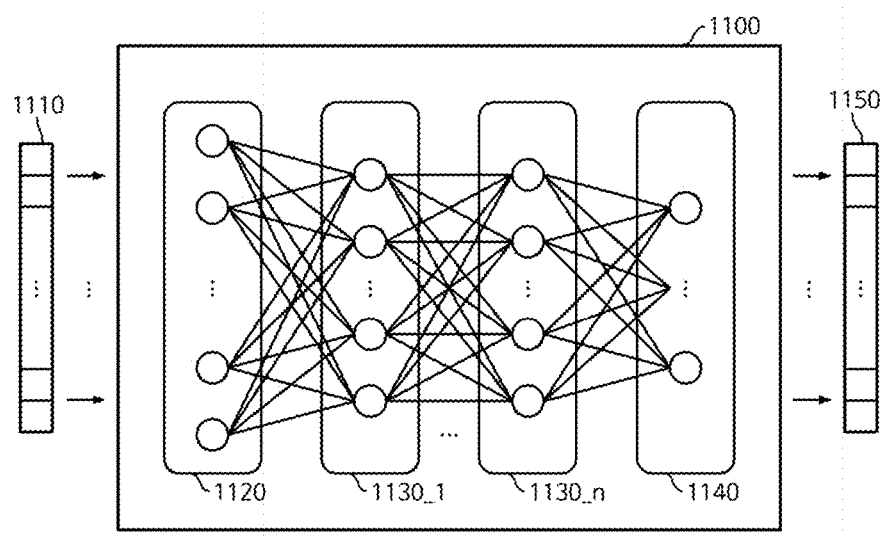
FIG. 11 illustrates an example of an artificial neural network model.

FIG. 11 illustrates an example of an artificial neural network model 1100. In machine learning technology and cognitive science, the artificial neural network model 1100 as an example of the machine learning model refers to a statistical learning algorithm implemented based on a structure of a biological neural network, or to a structure that executes such algorithm.

The artificial neural network model 1100 may represent a machine learning model that acquires a problem solving ability by repeatedly adjusting the weights of synapses by the nodes that are artificial neurons forming the network through synaptic combinations as in the biological neural networks, thus training to reduce errors between a target output corresponding to a specific input and a deduced output. For example, the artificial neural network model 1100 may include any probability model, neural network model, etc., that is used in artificial intelligence training methods such as machine learning and deep learning.

The cardio angiogram anatomical dominance determination model and SYNTAX score computation model described above may be generated in the form of the artificial neural network model 1100. For example, the artificial neural network model 1100 may receive a cardio angiogram and determine the anatomical dominance of the cardiovascular system in the cardio angiogram. As another example, the artificial neural network model 1100 may receive information corresponding to a specific frame of a cardio angiogram and a specific segment of the cardiovascular system, generate an analysis result for a lesion in the specific cardiovascular segment based on the information, and compute a SYNTAX score for at least a part of the cardiovascular system based on the analysis result.

The artificial neural network model 1100 is implemented as a multilayer perceptron (MLP) including a plurality of nodes and connections between the nodes. The artificial neural network model 1100 may be implemented using one of various artificial neural network model structures including the MLP. As illustrated in FIG. 11, the artificial neural network model 1100 includes an input layer 1120 to receive an input signal or data 1110 from the outside, an output layer 1140 to output an output signal or data 1150 corresponding to the input data, and (n) number of hidden layers 1130_1 to 1130_n (where n is a positive integer) positioned between the input layer 1120 and the output layer 1140 to receive a signal from the input layer 1120, extract the features, and transmit the features to the output layer 1140. In an example, the output layer 1140 receives signals from the hidden layers 1130_1 to 1130_n and outputs the signals to the outside.

The method of training the artificial neural network model 1100 includes the supervised learning that trains to optimize for solving a problem with inputs of teacher signals (correct answers), and the unsupervised learning that does not require a teacher signal. The information processing system may train the artificial neural network model 1100 using a plurality of cardio angiograms of the cardiovascular system.

The information processing system may directly generate the training data for training the artificial neural network model 1100. For example, the information processing system may generate a training data set including cardio angiograms. The information processing system may train the artificial neural network model 1100 for determining the anatomical dominance of cardiovascular system in cardio angiograms based on the generated training data set. In another example, the information processing system may generate a training data set including information of a specific frame and a specific segment of the cardiovascular system corresponding thereto. The information processing system may generate an analysis result of the lesion in the specific cardiovascular segment based on the generated training data set and train the artificial neural network model 1100 to compute a SYNTAX score for at least a part of the cardiovascular system based on the analysis result.

An input variable of the artificial neural network model 1100 may include a cardio angiogram. If the input variable described above is input through the input layer 1120, the output variable output from the output layer 1140 of the artificial neural network model 1100 may be the anatomical dominance of the cardiovascular system in the cardio angiogram. According to another aspect, the input variable of the artificial neural network model 1100 may include information of a specific frame and a specific segment of the cardiovascular system corresponding thereto. If the input variable described above is input through the input layer 1120, the output variable output from the output layer 1140 of the artificial neural network model 1100 may be an analysis result of the lesion in the specific cardiovascular segment and a SYNTAX score for at least a part of the cardiovascular system.

As described above, the input layer 1120 and the output layer 1140 of the artificial neural network model 1100 are respectively matched with a plurality of output variables corresponding to a plurality of input variables, and as the synaptic values between nodes included in the input layer 1120, and the hidden layers 1130_1 to 1130_n, and the output layer 1140 are adjusted, training can be processed to extract a correct output corresponding to a specific input. Through this training process, the features hidden in the input variables of the artificial neural network model 1100 can be confirmed, and the synaptic values (or weights) between the nodes of the artificial neural network model 1100 can be adjusted so that errors between the target output and the output variable calculated based on the input variable are reduced. The anatomical dominance of the cardiovascular in the received cardio angiogram may be determined using the artificial neural network model 1100 trained as described above. In addition, the analysis result for the lesion in the specific cardiovascular segment may be generated using the trained artificial neural network model 1100, and a SYNTAX score for at least a part of the cardiovascular system may be computed based on the analysis result.

The method described above may be provided as a computer program stored in a computer-readable recording medium for execution on a computer. The medium may be a type of medium that continuously stores a program executable by a computer, or temporarily stores the program for execution or download. In addition, the medium may be a variety of recording means or storage means having a single piece of hardware or a combination of several pieces of hardware, and is not limited to a medium that is directly connected to any computer system, and accordingly, may be present on a network in a distributed manner. An example of the medium includes a medium configured to store program instructions, including a magnetic medium such as a hard disk, a floppy disk, and a magnetic tape, an optical medium such as a CD-ROM and a DVD, a magnetic-optical medium such as a floptical disk, a ROM, a RAM, a flash memory, etc. In addition, other examples of the medium may include an app store that distributes applications, a site that supplies or distributes various software, and a recording medium or a storage medium managed by a server.

The methods, operations, or techniques of the present disclosure may be implemented by various means. For example, these techniques may be implemented in hardware, firmware, software, or a combination thereof. Those skilled in the art will further appreciate that various illustrative logical blocks, modules, circuits, and algorithm steps described in connection with the disclosure herein may be implemented in electronic hardware, computer software, or combinations of both. To clearly illustrate this interchangeability of hardware and software, various illustrative components, blocks, modules, circuits, and steps have been described above generally in terms of their functionality. Whether such a function is implemented as hardware or software depends on design requirements imposed on the particular application and the overall system. Those skilled in the art may implement the described functions in varying ways for each particular application, but such implementation should not be interpreted as causing a departure from the scope of the present disclosure.

In a hardware implementation, processing units used to perform the techniques may be implemented in one or more ASICs, DSPs, digital signal processing devices (DSPDs), programmable logic devices (PLDs), field programmable gate arrays (FPGAs), processors, controllers, microcontrollers, microprocessors, electronic devices, other electronic units designed to perform the functions described in the present disclosure, computer, or a combination thereof.

Accordingly, various example logic blocks, modules, and circuits described in connection with the present disclosure may be implemented or performed with general purpose processors, DSPs, ASICs, FPGAs or other programmable logic devices, discrete gate or transistor logic, discrete hardware components, or any combination of those designed to perform the functions described herein. The general purpose processor may be a microprocessor, but in the alternative, the processor may be any related processor, controller, microcontroller, or state machine. The processor may also be implemented as a combination of computing devices, for example, a DSP and microprocessor, a plurality of microprocessors, one or more microprocessors associated with a DSP core, or any other combination of the configurations.

In the implementation using firmware and/or software, the techniques may be implemented with commands stored on a computer-readable medium, such as random access memory (RAM), read-only memory (ROM), non-volatile random access memory (NVRAM), programmable read-only memory (PROM), erasable programmable read-only memory (EPROM), electrically erasable PROM (EEPROM), flash memory, compact disc (CD), magnetic or optical data storage devices, etc. The commands may be executable by at least one processor, and may cause the processor(s) to perform certain aspects of the functions described in the present disclosure.

When implemented in software, the techniques may be stored on a computer-readable medium as one or more instructions or codes, or may be transmitted through a computer-readable medium. The computer-readable media include both the computer storage media and the communication media including any medium that facilitates the transmission of a computer program from one place to another. The storage media may also be any available media that may be accessible to a computer. By way of non-limiting example, such a computer-readable medium may include RAM, ROM, EEPROM, CD-ROM or other optical disk storage, magnetic disk storage or other magnetic storage devices, or any other media that can be used to transmit or store desired program code in the form of instructions or data structures and can be accessible to a computer. In addition, any connection is properly referred to as a computer-readable medium.

For example, if the software is sent from a website, server, or other remote sources using coaxial cable, fiber optic cable, twisted pair, digital subscriber line (DSL), or wireless technologies such as infrared, wireless, and microwave, the coaxial cable, the fiber optic cable, the twisted pair, the digital subscriber line, or the wireless technologies such as infrared, wireless, and microwave are included within the definition of the medium. The disks and the discs used herein include CDs, laser disks, optical disks, digital versatile discs (DVDs), floppy disks, and Blu-ray disks, where disks usually magnetically reproduce data, while discs optically reproduce data using a laser. The combinations described above should also be included within the scope of the computer-readable media.

The software module may reside in RAM memory, flash memory, ROM memory, EPROM memory, EEPROM memory, registers, hard disk, removable disk, CD-ROM, or any other form of storage medium known. An exemplary storage medium may be connected to the processor such that the processor may read or write information from or to the storage medium. Alternatively, the storage medium may be integrated into the processor. The processor and the storage medium may be present in the ASIC. The ASIC may be present in the user terminal. Alternatively, the processor and storage medium may exist as separate components in the user terminal.

Although the examples described above have been described as utilizing aspects of the currently disclosed subject matter in one or more standalone computer systems, aspects are not limited thereto, and may be implemented in conjunction with any computing environment, such as a network or distributed computing environment. Furthermore, the aspects of the subject matter in the present disclosure may be implemented in multiple processing chips or devices, and storage may be similarly influenced across a plurality of devices. Such devices may include PCs, network servers, and portable device.

Although the present disclosure has been described in connection with some aspects herein, various modifications and changes can be made without departing from the scope of the present disclosure, which can be understood by those skilled in the art to which the present disclosure pertains. In addition, such modifications and changes should be considered within the scope of the claims appended herein.

The invention claimed is:

1. A method for computing a SYNTAX score using a cardio angiogram, the method being performed by at least one processor of a computing device and comprising:
   acquiring an angiogram of a cardiovascular system;
   providing a cardiovascular segment map associated with the angiogram;
   in response to a user input that selects one of one or more frames included in the acquired angiogram and associates the selected one frame with a cardiovascular segment included in the cardiovascular segment map, associating the selected one frame with the cardiovascular segment;
   generating, using the selected one frame, an analysis result for a lesion in the associated cardiovascular segment;
   determining, based on the analysis result, a SYNTAX score for at least a part of the cardiovascular system;
   generating an indication of the SYNTAX score; and
   outputting, on the cardiovascular segment map, the indication of the SYNTAX score and the selected one frame in association with the cardiovascular segment.

2. The method of claim 1, wherein the providing the cardiovascular segment map comprises:
   determining, based on the acquired angiogram, an anatomical dominance of the angiogram; and
   providing a cardiovascular segment map associated with the anatomical dominance of the angiogram.

3. The method according to claim 2, wherein the determining the anatomical dominance of the angiogram comprises determining, based on the acquired angiogram, the anatomical dominance of the angiogram using a machine learning model trained to determine an anatomical dominance of a given angiogram.

4. The method according to claim 1, wherein the determining the SYNTAX score comprises:
   generating an analysis result for a lesion in each of one or more sub-segments of the associated cardiovascular segment; and
   determining, based on the generated analysis result, a SYNTAX score for at least a part of the cardiovascular system.

5. The method according to claim 1, wherein the determining the SYNTAX score comprises:
   in response to determining that the lesion in the cardiovascular segment comprises chronic total occlusion (CTO), analyzing the lesion in the associated cardiovascular segment to determine a SYNTAX score for the at least part of the cardiovascular system, without analyzing a sub-segment of the cardiovascular segment.

6. A method for providing a SYNTAX score using a cardio angiogram, the method being performed by at least one processor of a computing device and comprising:
   receiving an angiogram of a cardiovascular system;
   outputting one or more frames included in the received angiogram;
   outputting a cardiovascular segment map associated with the angiogram;
   receiving a user input that selects one frame from among the one or more frames and associates the frame with a cardiovascular segment included in the cardiovascular segment map, wherein the receiving the user input comprises receiving a user input by a drag and drop method, and wherein the user input positions the selected one frame on a specific cardiovascular segment included in the cardiovascular segment map;
   in response to the user input, associating the selected one frame with the cardiovascular segment; and
   outputting a SYNTAX score for at least a part of the cardiovascular system, wherein the SYNTAX score is determined based on a result of analyzing a lesion in the cardiovascular segment using the selected one frame.

7. The method according to claim 6, further comprising:
   extracting, from the one or more frames, a frame associated with one cardiovascular segment included in the cardiovascular segment map; and
   outputting the extracted frame as a recommended frame of the cardiovascular segment.

8. The method according to claim 6, further comprising:
   in response to determining that the selected one frame and the cardiovascular segment have an association value that is equal to or less than a threshold, extracting, from the one or more frames, a frame associated with the cardiovascular segment included in the cardiovascular segment map; and
   outputting the extracted frame as a recommended frame of the cardiovascular segment.

9. The method according to claim 6, wherein the outputting the cardiovascular segment map comprises outputting a cardiovascular segment map associated with an anatomical dominance of the angiogram.

10. The method according to claim 6, wherein the outputting the SYNTAX score comprises outputting, on the cardiovascular segment map, the selected one frame in association with the cardiovascular segment.

11. The method according to claim 6, wherein:
    a result of analyzing a lesion in each of one or more sub-segments of the associated cardiovascular segment is generated using the selected one frame, and
    the outputting the SYNTAX score comprises outputting the cardiovascular segment and the one or more sub-segments, for which an analysis result of the lesion is generated, in a predetermined format.

12. A non-transitory computer-readable medium storing instructions that, when executed, cause performance of the method according to claim 1.

13. A computing device, comprising:
    a memory; and
    at least one processor coupled to the memory and configured to execute at least one computer-readable program included in the memory, wherein
    the at least one program comprises instructions that, when executed by the at least one processor, cause the computing device to:
    acquire an angiogram of a cardiovascular system;
    provide a cardiovascular segment map associated with the angiogram;
    in response to a user input that selects one frame from among one or more frames included in the acquired angiogram and associates the selected one frame with a cardiovascular segment included in the cardiovascular segment map, associate the selected one frame with the cardiovascular segment;

generate, using the selected one frame, an analysis result for a lesion in the associated cardiovascular segment;

determine, based on the analysis result, a SYNTAX score for at least a part of the cardiovascular system;

generate an indication of the SYNTAX score; and output, on the cardiovascular segment map, the indication of the SYNTAX score and the selected one frame in association with the cardiovascular segment.

14. The computing device of claim 13, wherein the instructions, when executed by the at least one processor, cause the computing device to provide the cardiovascular segment map by:

determining, based on the acquired angiogram, an anatomical dominance of the angiogram; and providing a cardiovascular segment map associated with the anatomical dominance of the angiogram.

15. The computing device of claim 14, wherein the instructions, when executed by the at least one processor, cause the computing device to determine the anatomical dominance of the angiogram by determining, based on the acquired angiogram, the anatomical dominance of the angiogram using a machine learning model trained to determine an anatomical dominance of a given angiogram.

16. The computing device of claim 13, wherein the instructions, when executed by the at least one processor, cause the computing device to determine the SYNTAX score by:

generating an analysis result for a lesion in each of one or more sub-segments of the associated cardiovascular segment; and determining, based on the generated analysis result, a SYNTAX score for at least a part of the cardiovascular system.

17. The computing device of claim 13, wherein the instructions, when executed by the at least one processor, cause the computing device to determine the SYNTAX score by:

in response to determining that the lesion in the cardiovascular segment comprises chronic total occlusion (CTO), analyzing the lesion in the associated cardiovascular segment to determine a SYNTAX score for the at least part of the cardiovascular system, without analyzing a sub-segment of the cardiovascular segment.

18. The computing device of claim 13, wherein the instructions, when executed by the at least one processor, cause the computing device to:

in response to determining that the selected one frame and the cardiovascular segment have an association value that is equal to or less than a threshold, extracting, from the one or more frames, a frame associated with the cardiovascular segment included in the cardiovascular segment map.

* * * * *